(12) United States Patent
Masson et al.

(10) Patent No.: US 8,475,848 B2
(45) Date of Patent: Jul. 2, 2013

(54) COSMETIC COMPOSITION HAVING ANTI-RADICAL PROPERTIES AND CORRESPONDING APPLICATION METHOD

(75) Inventors: Stéphane Jacques Joseph Masson, Compiegne (FR); Anne Marie Catherine Simonnet, Compiegne (FR); Anne Marie Guillemette De La Sayette, La Rochelle (FR); Christine Anne-Maria Raymonde Brunet, La Jarne (FR)

(73) Assignee: Yves Saint Laurent Parfums, Neuilly sur Seine (FR)

( * ) Notice: Subject to any disclaimer, the term of this patent is extended or adjusted under 35 U.S.C. 154(b) by 57 days.

(21) Appl. No.: 12/452,458

(22) PCT Filed: Jul. 3, 2008

(86) PCT No.: PCT/FR2008/000949
§ 371 (c)(1),
(2), (4) Date: Jun. 7, 2010

(87) PCT Pub. No.: WO2009/024671
PCT Pub. Date: Feb. 26, 2009

(65) Prior Publication Data
US 2010/0247464 A1    Sep. 30, 2010

(30) Foreign Application Priority Data
Jul. 6, 2007    (FR) ..................... 07 04925

(51) Int. Cl.
*A01N 65/00*    (2009.01)

(52) U.S. Cl.
USPC .......................................... 424/725

(58) Field of Classification Search
None
See application file for complete search history.

(56) References Cited

U.S. PATENT DOCUMENTS

| 4,268,265 | A  | 5/1981  | Von Wattenwyl |
| 2006/0280762 | A1 | 12/2006 | Kostick et al. |

FOREIGN PATENT DOCUMENTS

| FR | 2 432 035 A  | 2/1980 |
| WO | WO 99/11718  | 3/1999 |
| WO | WO 01/55263  | 8/2001 |
| WO | WO 2006/136880 | 12/2006 |

OTHER PUBLICATIONS

International Search Report mailed on Dec. 9, 2009, for PCT International Application No. PCT/FR2008/000949, filed Jul. 3, 2008.
International Preliminary Report on Patentability issued Jan. 12, 2010 in connection with PCT International Application No. PCT/FR2008/000949, filed Jul. 3, 2008.
Written Opinion of the International Searching Authority issued on Jan. 6, 2010 in connection with International Application No. PCT/FR2008/000949, filed Jul. 3, 2008.

*Primary Examiner* — Michael Meller
(74) *Attorney, Agent, or Firm* — John P. White; Cooper & Dunham LLP

(57) ABSTRACT

The invention provides a cosmetic composition for topical use having anti-radical properties and including at least one plant extract of natural origin in a cosmetically acceptable medium, the composition being characterized in that said at least one plant extract of natural origin is insoluble.

2 Claims, 3 Drawing Sheets

COSMETIC COMPOSITION HAVING ANTI-RADICAL PROPERTIES AND CORRESPONDING APPLICATION METHOD

This application is a §371 national stage of PCT International Application No. PCT/FR2008/000949, filed Jul. 3, 2008, claiming priority of French Patent Application No. 0704925, filed Jul. 6, 2007, the contents of all of which are hereby incorporated by reference into this application.

FIELD OF THE INVENTION

The present invention relates to the general technical field of cosmetic products for topical use, in particular for use on the skin, the hair, and the nails, and in particular that may be in the fluid or liquid, paste, semi-liquid or semi-paste, gel, powder, or mousse form.

In particular, the present invention relates to the general technical field of cosmetic products containing anti-radical substances endowing them with anti-radical properties.

The present invention provides a cosmetic composition for topical use having anti-radical properties and comprising at least one plant extract of natural origin in a cosmetically acceptable medium.

The present invention also provides the use of a plant extract of natural origin in a cosmetic composition having anti-radical properties.

Finally, the present invention provides a method of applying a cosmetic composition for topical use having anti-radical properties.

In its preferred application, the cosmetic composition in accordance with the invention constitutes makeup for the skin, the nails, and the hair, and presenting anti-radical properties.

PRIOR ART

In general, the parts of the human organism in contact with the environment in the broad sense, and in particular the skin, the hair, and the nails, are the most sensitive to external elements that may have harmful effects.

Further, the skin is particularly vulnerable to free radical attacks. These oxidizing molecules may prove to be dangerous in excess, and in particular they play an important role in skin ageing.

Free radicals, generated by the normal function of the human organism, are generally balanced with anti-oxidizing molecules. The natural anti-oxidizing defense mechanisms of the skin involve molecules such as vitamin E, vitamin C, selenium, enzymes etc. The principal property of such anti-oxidizing molecules is trapping free radicals from the organism with a view to maintaining the equilibrium between the free radicals and the anti-oxidizing molecules.

Free radicals are also produced under the influence of external elements such as pollution, tobacco, or UV radiation. In certain situations, the density of the anti-oxidants reduces while the number of free radicals increases. The natural equilibrium between the free radicals and the anti-oxidizing molecules is then disturbed, creating an oxidative stress. That stress renders them aggressive towards the organism, in particular as regards the fundamental elements of the skin, such as keratinocytes, fibroblasts, collagen, or elastin, in particular. Attack of the skin by free radicals has many consequences; the most frequent are its loss of solidity and elasticity.

Thus, there is a distinct interest in providing the skin in particular with substances having anti-radical properties to strengthen its natural defenses and to aid in combating free radicals.

The demand for cosmetic products is constantly increasing and there is currently, moreover, a trend towards promoting products that protect the skin and other surfaces of the body that are exposed to external elements. It turns out that consumers would like to use a cosmetic product, in particular a makeup product, which also actually cares for the skin. The basic properties of a makeup product, namely to provide color, to camouflage and to correct minor skin imperfections, can henceforth be supplemented by biological properties, for example to protect the skin from free radicals.

It also turns out that products conveying a "natural" image are in particular demand. As opposed to certain synthetic compounds that are incorporated into cosmetic compositions, products of natural origin or containing natural compounds are becoming more and more valued by consumers.

These various reasons have persuaded the cosmetics industry to bring onto the cosmetics market products containing natural substances or substances of natural origin that have anti-radical properties in order to satisfy the above-mentioned trend in particular.

For this reason, cosmetic compositions are already known that contain such substances that can trap free radicals that are produced in excess by the organism during external attack (pollution, tobacco, UV, etc).

Such compositions conventionally contain at least one anti-oxidizing substance, in particular of plant origin, such as an anthocyanin. Anthocyanin is in general incorporated in the pure state or in the form isolated from a plant extract.

However, such purified molecules are often synthesized molecules that may in particular be obtained using biotechnology. Thus, in the consumers' eyes they are no longer associated with the image of natural products.

Further, there are difficulties associated with low market availability of plant extracts of natural origin that can be incorporated into cosmetic compositions, in particular into anhydrous makeup compositions, thereby further limiting their use.

Thus, it is currently difficult to obtain cosmetic compositions, in particular makeup products, that have anti-radical properties and that contain a plant extract of natural origin even though the need is great.

SUMMARY OF THE INVENTION

As a consequence, the invention aims to overcome the various difficulties set out above by proposing a novel cosmetic composition having anti-radical properties and containing at least one plant extract of natural origin that may be incorporated into cosmetic compositions readily and on a large scale.

A further aim of the invention is to propose a novel cosmetic composition that can provide an anti-radical action that is particularly simple and effective.

A further aim of the invention is to propose a novel cosmetic composition incorporating natural compounds derived from plants that exist widely in the natural state and that are readily available.

A further aim of the invention is to propose a novel cosmetic composition offering broad scope for incorporating substances with anti-radical properties.

A further aim of the invention is to propose a novel cosmetic composition having a wide spectrum of application and use in the cosmetics field.

A further aim of the invention is to propose a novel use of a plant extract of natural origin in a cosmetic composition for topical use.

A further aim of the invention is to propose a novel method of applying a cosmetic composition for topical use having anti-radical properties.

The stated aims of the invention are achieved by means of a cosmetic composition for topical use having anti-radical properties and including at least one plant extract of natural origin in a cosmetically acceptable medium, the composition being characterized in that said at least one plant extract of natural origin is insoluble.

The stated aims of the invention are also achieved by means of the use of at least one insoluble plant extract of natural origin as an anti-radical agent in a cosmetic composition for topical use to provide it with anti-radical properties.

The stated aims of the invention are also achieved by means of a method of applying a cosmetic composition for topical use intended to protect the epidermis, nails, and hair against free radicals, the method being characterized in that it consists in applying a cosmetic composition as defined above to said epidermis, nails and hair.

Further details of other advantages and aims of the invention become apparent from the following description and with the aid of examples and tests that are provided purely by way of non-limiting illustration.

BEST MANNER OF CARRYING OUT THE INVENTION

The invention provides a cosmetic composition defined in accordance with the invention as a composition intended for cleansing, protecting, fragrancing, keeping the human body in good condition, and modifying the appearance and/or the odor of the human body.

A cosmetic composition as defined in the invention may thus be a hygiene product (toothpaste, deodorant, shower gel, soap, shampoo), a skin care product (anti-wrinkle cream, day cream, night cream, moisturizing cream, flower water, gommage, milk, beauty mask, lip balm, tonic), a hair product (conditioner, straightener, gel, oil, lacquer, mask, dye), a fragrance (eau de cologne, toilet water, perfume), a makeup product (concealer, self-tanning agent, eyeliner, eye shadow, foundation, kohl, mascara, powder, skin bleaching product, lipstick and/or nail polish) and/or a sun product (creams, oils or after-sun lotions and sun lotions).

The invention provides a cosmetic composition for topical use, i.e. acting at the location where it is applied, namely to an external surface of the body.

The invention provides a cosmetic composition defined in a cosmetically acceptable medium. The term "cosmetically acceptable medium" means a set of ingredients that are well known to the skilled person that may be mixed while having regard to the constraints applicable to the use of each individual ingredient, the constraints linked to possible interactions between the ingredients, and the legislative constraints associated with certain ingredients (maximum dose that can be incorporated, etc). Any ingredient in routine use in cosmetic compositions may thus constitute a cosmetically acceptable medium in the context of the invention, provided that the above constraints are respected.

The composition of the invention has anti-radical properties. The term "anti-radical" as used in the context of the invention means "having an action against free radicals naturally produced by the human organism". In other words, the anti-radical property is an anti-oxidizing property associated with a substance or a compound. An anti-oxidizing substance is capable of reducing or preventing oxidation of other chemical substances of the organism, said oxidation reaction producing free radicals that may entrain destructive chain reactions. Anti-oxidants are capable of stopping such chain reactions by being oxidized by the free radicals, thereby eliminating their action.

In accordance with the invention, the cosmetic composition can reduce the quantity of free radicals by neutralizing the excess produced by the organism in the event of external stress (pollution, solar radiation, stress, tobacco, alcohol, etc).

The present invention provides a cosmetic composition including at least one plant extract of natural origin. Within the context of the present invention, the plant extract of natural origin is a preparation obtained by maceration of all or a portion of a plant in a liquid solvent and by subsequently evaporating off the solvent. The term "plant extract of natural origin" means a plant extract derived from extraction from a plant that is found in nature or cultivated. The constituent molecules of the plant extract of natural origin are themselves of natural origin, as opposed to synthesized molecules.

The invention provides a cosmetic composition for topical use having anti-radical properties and including at least one natural plant extract in a cosmetically acceptable medium, characterized in that said at least one plant extract of natural origin is insoluble. The term "insoluble plant extract of natural origin" means a plant extract of natural origin that cannot be dissolved, or cannot be substantially dissolved in water, in an aqueous medium or in an oily medium. In other words, the plant extract of the present invention is substantially insoluble in the cosmetic medium into which it is incorporated. Because of this technique, it is particularly easy to incorporate the plant extract of natural origin into a cosmetic composition, in particular into an anhydrous cosmetic composition or a composition containing very little water, such as into makeup products, in particular because of the very good compatibility of the insoluble plant extract of natural origin with the other components of said anhydrous cosmetic composition.

Preferably, in the invention said at least one plant extract of natural origin contains at least one anti-radical substance. In other words, said at least one plant extract of natural origin contains a substance that is capable of returning the unusually large quantity of free radicals arising from external influences (pollution, solar radiation, stress, tobacco, alcohol, etc) to or close to its natural equilibrium in the organism.

In a variation, the anti-radical substance may be contained in a component of the composition other than the plant extract of natural origin without departing from the scope of the invention.

In accordance with the invention, said at least one anti-radical substance described above is a polyphenol, a natural anti-oxidant constituting a family of organic molecules that is plentiful in the realm of plants. Polyphenols, produced by the secondary metabolism of plants, are characterized by the presence of several phenol groups associated with structures of varying complexity, with a high molecular weight. They are natural anti-oxidants divided into several sub-families that may be incorporated, alone or in combination, into the composition of the invention; examples are phenolic acids, flavanones, tannins, and anthocyanins.

However, the scope of the invention also encompasses anti-oxidants with an origin other than polyphenols. In particular, they may be vitamin C, vitamin E, enzymes, and/or carotenoids. Alternatively, the use of anti-oxidants of animal origin that also have a recognized anti-radical action may also be envisaged.

Advantageously, in the cosmetic composition according to the invention, said at least one plant extract of natural origin derives from extraction from plants selected from those containing polyphenols.

In accordance with the invention, said at least one plant extract of natural origin derived from extraction from plants containing polyphenols is preferably selected from plant extracts containing at least one or more of the following molecules: fustin, dihydrorobinetin, brazilin, brazilein, sulfuretin, sulfurein (sulfuretin 6-glucoside), palasitrin (sulfuretin 3',6-diglucoside), coreopsin (butein 4'-glucoside), apigeninidin, luteolinidin, cyanidin, pelargonidin, fisetinidin, gallic acid, ellagic acid, valonic acid, proanthocyanidols and profisetinidin.

These molecules with a polyphenolic nature belong to various biochemical families of polyphenols including flavonoids, anthocyanins and tannins. A non-limiting list is given below; they may be used in a cosmetic composition in accordance with the invention:

Flavonoids

The flavonoids include neo-flavonoids, chalcones, aurones, flavanones, flavonols, and flavanols. The general formula for flavanones is as follows:

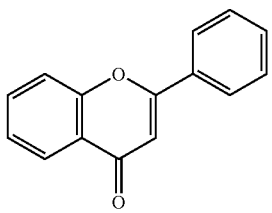

The flavonoids include fustin and dihydrorobinetin in particular. Brazilin is the principal molecule of the neo-flavonoid family and is transformed into red brazilein by oxidation.

The aurones, the other flavonoid sub-family, includes in particular sulfuretin, sulfurein (sulfuretin 6-glucoside) and palasitrin (sulfuretin 3',6-diglucoside).

Coreopsin (butein 4'-glucoside) belongs to the flavonoid family but forms part of the chalcone family of biochemicals.

Anthocyanins:

The general formula for anthocyanins is as follows:

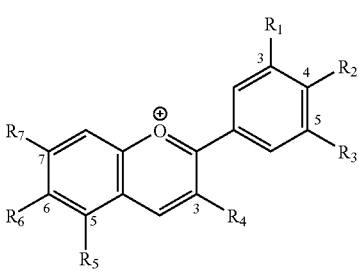

in which R1, R2, R3, R4, R5, R6 and R7=H, OH, or OCH$_3$.

Apigeninidin, luteolinidin, cyanidin, pelargonidin, and fisetinidin also form part of the anthocyanins family and have the following formulae:

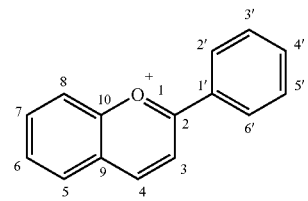

in which:

|  | 3 | 5 | 6 | 7 | 3' | 4' | 5' |
| --- | --- | --- | --- | --- | --- | --- | --- |
| Apigeninidin | H | OH | H | OH | H | OH | H |
| Luteolinidin | H | OH | H | OH | OH | OH | H |
| Cyanidin | OH | OH | H | OH | OH | OH | H |
| Pelargonidin | OH | OH | H | OH | H | OH | H |
| Fisetinidin | OH | H | H | OH | OH | OH | H |

Tannins:

Tannins, derivatives of gallic acid, and other polyphenolic acids, have a highly variable chemical structure which, however, always includes a polyphenolic portion. Certain tannins are termed hydrolysable tannins and produce either gallic acid or ellagic acid after hydrolysis.

Gallic acid forms part of the hydrolysable tannin family, especially the ellagic tannin family. Ellagic acid and valonic acid also belong to the ellagitannin family.

Other tannins are condensed tannins. These are polymers resulting from the condensation of flavan-3-ol units and their general formula is as follows:

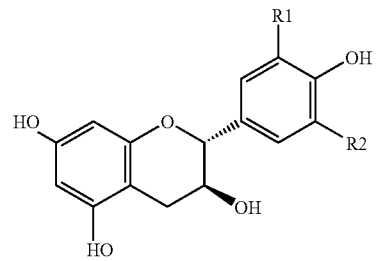

in which R1 and R2=H or OH (catechols or gallocatechols).

Proanthocyanidols form part of the condensed tannin family. This family includes profisetinidin in particular.

In accordance with the invention, the cosmetic composition of the invention preferably contains at least one plant extract of natural origin derived from the extraction from tinctorial plants.

Advantageously, said at least one plant extract of natural origin is derived from extraction from at least one plant selected from Cosmos, Pernambuco, Oak, Quebracho, and Sorghum, containing one or more anti-radical molecules as defined above. The concentration of polyphenols in these plants is greater than that conventionally found in the majority of plants.

Cosmos is an annual plant that originates in Mexico that contains flavonoids (aurones and chalcones), in particular sulfuretin, sulfurein (sulfuretin 6-glucoside), palasitrin (sulfuretin 3',6-diglucoside), and coreopsin (butein 4'-glucoside).

In accordance with the invention, the Pernambuco extract used derives from a tree from the Leguminosae family that is found in particular in Brazil in the province of Pernambuco.

Sawdust is recovered to manufacture the extract as used in the cosmetic composition of the invention. Preferably, the Pernambuco extract contains brazilin and red brazilein.

Oak extract, used in the cosmetic composition of the invention, is advantageously derived from the acorn cups. The cups from the Oak species used to manufacture the extract of the invention in the composition of the invention are the size of an apple and very rich in tannins, in particular in ellagic acid and in valonic acid.

The Quebracho is a tree the name of which derives from the Spanish quiebra hacha (axe breaker) due to its very hard wood. It is found in South America. The extract obtained from this tree and used in the cosmetic composition according to the invention is particularly rich in tannins and in flavonoids. Quebracho tannins are also used as additives in oenology. The brown color of the Quebracho extract is a mixture of hydrolysable tannins, in particular gallic acid and ellagic acid, which is principally found in its glycosylated form, and of condensed tannins, in particular profisetinidin.

Sorghum, as used in the invention, is an annual graminaceous plant, the "colorants" variety of which is used as dyes in Africa and has been found in thousand year old archeological strata. The two races of bicolor African Sorghum that are the most widely used for their colorant properties (food and cosmetic dyes) are Caudatum and Kafir. Sorghum extract is constituted by a mixture of flavonoids from the anthocyanidin group that is found in the free, glycosylated, or methoxylated form, and of condensed tannins, in particular fustin, dihydrobinetin, sulfuretin, apigeninidin, luteolinidin, cyanidin, pelargonidin, and fisetinidin.

Preferably, the cosmetic composition according to the invention may contain one or the other of said extracts as defined above or a mixture of several extracts derived from at least two of said plants.

The context of the invention also encompasses envisaging the use of extracts derived from plants other than those mentioned above. Any plants that naturally contain anti-oxidant molecules, especially polyphenols, may be used for extraction and incorporation into a cosmetic composition in accordance with the invention.

In accordance with the cosmetic composition of the invention, said at least one plant extract of natural origin represents substantially in the range 0.01% to 50% of the total cosmetic composition weight, preferably substantially in the range 0.5% to 20%.

In accordance with the cosmetic composition according to the invention, said at least one plant extract of natural origin represents substantially in the range 0.5% to 45% of the total cosmetic composition weight when said cosmetic composition is in a dry pulverulent form of the pressed powder type, in particular in a cosmetic eye shadow composition.

Alternatively, when said at least one plant extract of natural origin is introduced into a cosmetic composition with an anhydrous pasty formulation, its concentration is preferably substantially in the range 0.5% to 15% of the total cosmetic composition weight.

In accordance with the invention, when said at least one plant extract of natural origin is introduced into a cosmetic composition according to the invention taking the form of an emulsion, its concentration is preferably substantially in the range 0.01% to 20% of the total cosmetic composition weight.

In a preferred embodiment of the invention, the cosmetic composition includes a mixture of plant extracts of natural origin derived from extraction from at least two plants selected from Cosmos, Pernambuco, Oak, Quebracho and Sorghum, in total representing substantially 0.01% to 50% of the total cosmetic composition weight, more particularly substantially in the range 0.5% to 20% of the cosmetic composition weight.

The plant extracts obtained at the end of conventional extraction methods and starting from the plants described above are naturally hydrosoluble, very difficult to handle and difficult if not impossible to incorporate in anhydrous cosmetic makeup product compositions.

In the present invention, said at least one plant extract of natural origin of the cosmetic composition is coupled with a mineral substrate, preferably calcium carbonate. Alternatively, any other insoluble mineral substrate may be coupled with said at least one plant extract of natural origin to render it insoluble. In other words, the combination of the plant extract with a mineral substrate contributes to rendering the plant extract substantially insoluble in the medium into which it is introduced. The use of plant extracts of natural origin that are insoluble in cosmetic compositions facilitates their incorporation into said compositions and in particular into anhydrous compositions or those containing very little water. This coupling of a natural plant extract with a natural substrate is carried out in a manner that is sufficiently secure to prevent the plant extract from subsequently leaching out in the cosmetic composition into which it is incorporated.

Preferably, the cosmetic composition according to the invention protects the epidermis against free radicals. In particular, the cosmetic composition is in the form of an emulsion and/or cream and/or gel and/or body milk and/or powder and/or lotion and/or mask and/or balm that could be applied to the human epidermis.

Alternatively, the cosmetic composition according to the invention protects the hair against free radicals. In this variation of the invention, the cosmetic composition is preferably in the form of a shampoo and/or conditioner and/or gel and/or oil and/or spray and/or protector and/or colored hair treatment and/or hair repair treatment and/or lotion and/or lacquer, suitable for application to the hair.

Alternatively, the cosmetic composition according to the invention may be envisaged as protecting the nails against free radicals and is preferably in the form of a treatment and/or repair treatment and/or nail polish and/or nail base for polish.

In a preferred embodiment of the invention, the cosmetic composition constitutes a makeup product for the skin and/or the hair and/or the eyelashes and/or the eyebrows and/or the nails. Preferably, said cosmetic composition is in the form of cream for improving the epidermis and/or lipstick and/or eye shadow and/or powder and/or mascara and/or liquid foundation and/or powder foundation and/or mousse foundation and/or crayon and/or blusher and/or eyeliner and/or nail polish. Alternatively, and within the scope of the invention, said cosmetic composition may be in any other form of makeup product normally used for topical application, preferably in the form of an anhydrous composition containing very little or no water.

EXAMPLES

By way of illustration of the invention, four examples of formulations of makeup products presented in some of the galenical forms described above are given below and illustrate the above description in more detail. These examples are provided purely by way of non-limiting illustration. The ingredients in each of the examples are expressed as a percentage of the total cosmetic composition weight.

Example 1

Eye Shadow Formulation Containing Insoluble Plant Extracts of Natural Origin

| | |
|---|---|
| Talc | 4 |
| Magnesium stearate | 0.5 |
| Mica | 25.75 |
| Aluminum starch octenyl succinate | 10 |
| Nylon-12 | 5 |
| Cetrimonium bromide | 0.1 |
| Methylparaben | 0.1 |
| Insoluble Quebracho plant extract | 15 |
| Insoluble Cosmos plant extract | 15 |
| Insoluble Pernambuco plant extract | 20 |
| Dimethicone | 4.5 |
| Tocopherol | 0.05 |

In this anhydrous dry pulverulent eye shadow formulation, the insoluble plant extracts of natural origin were introduced in an amount of 50% of the total dry composition weight. This percentage was much higher than the percentages of non-insoluble plant extracts incorporated into cosmetic compositions.

Example 2

Lipstick Formulation Containing Insoluble Plant Extracts of Natural Origin

| | |
|---|---|
| Polyethylene | 9 |
| Microcrystalline wax | 7 |
| Polybutene | 25 |
| Octyldodecanol | 15 |
| Butyloctyl salicylate | 24 |
| Propylparaben | 0.1 |
| Silica | 0.5 |
| Tocopherol | 0.5 |
| Candellila wax | 2.85 |
| Ethylhexylmethoxycinnamate | 4 |
| Fragrance | 0.05 |
| Pentaerythrityl tetraisostearate | 6 |
| Insoluble Pernambuco plant extract | 3 |
| Insoluble Quebracho plant extract | 3 |

In this conventional lipstick formula, the insoluble plant extracts of natural origin were introduced in an amount of 6% of the total dry composition weight.

Example 3

Foundation Formulation

| | |
|---|---|
| Water | 62.8 |
| Cyclopentacyloxane & PEG-PPG 18-18 dimethicone | 8 |
| Cyclomethicone | 9 |
| Disteardimonium hectorite & propylene carbonate & cyclopentasiloxane | 1 |
| Phenoxyethanol & parabens | 1 |
| Fragrance | 0.2 |
| Sodium chloride | 2 |
| Glycerin | 3 |
| Silica | 2 |
| Insoluble Quebracho plant extract | 4 |
| Insoluble Cosmos plant extract | 2 |
| Titanium dioxide | 5 |

In this conventional foundation formula, the insoluble plant extracts of natural origin were introduced in an amount of 6% of the total dry composition weight.

Example 4

Face Cream Formulation

| | |
|---|---|
| Water | 80.4 |
| Tetrasodium EDTA | 0.1 |
| Hydroxypropyl starch phosphate | 5 |
| *Glycine soya* | 1 |
| Stearic acid | 1.5 |
| Cetyl alcohol | 0.5 |
| Glycerin | 5 |
| Sorbitan stearate | 0.5 |
| Polysorbate 60 | 0.4 |
| Capric/caprylic triglycerides | 3 |
| Triethanolamine | 0.5 |
| Phenoxyethanol & parabens | 1 |
| Fragrance | 0.2 |
| Tocopherol acetate | 0.5 |
| Insoluble Pernambuco plant extract | 0.4 |

In this face cream formula, the single insoluble plant extract of natural origin represented 0.4% of the total dry composition weight.

It should be noted that in Examples 3 and 4 the compositions contained respectively 62.8% and 80.4% of water, which rendered these compositions aqueous in nature and no longer anhydrous as in Examples 1 and 2. The present invention can thus equally allow insoluble plant extracts of natural origin to be introduced into anhydrous cosmetic compositions of the makeup product type and/or into cosmetic compositions containing larger or smaller quantities of water.

The list of ingredients in the cosmetic compositions of the examples given above is not exhaustive. The cosmetic formulation involves a large number of ingredients. The invention is clearly not limited to certain of these ingredients in particular and any known ingredient may be introduced into a cosmetic composition. The cosmetic composition should naturally clearly be adapted to the galenical form of the makeup product.

The invention also provides the use of at least one insoluble plant extract of natural origin as an anti-radical agent in a cosmetic composition for topical use in order to endow it with anti-radical properties. This use in accordance with the invention is preferably intended to protect the epidermis, nails, and hair against environmental pollution in all its forms (UV radiation, tobacco, toxic gas, etc), and in particular against free radicals that are produced naturally in excess by the organism when under external stress.

Lastly, the invention provides a method of applying a cosmetic composition for topical use intended to protect the epidermis, the nails and the hair against free radicals, the method being characterized in that it consists in applying a cosmetic composition as defined above to said epidermis, nails, and hair. The cosmetic composition of the invention is applied in a manner that is routine as regards cosmetic products. In particular, the cosmetic composition according to the invention may be applied manually or using a conventional tool (brush, glove, comb, spatula, spray, paint brush, cotton wool, etc).

Advantageously, the anti-radical properties of the plant extracts of natural origin described in the present invention were tested in tests that are detailed below.

Anti-Radical Effectiveness Tests

1. Tests on Plant Extract.

The anti-radical properties of the plant extracts of natural origin used in the compositions of the invention were demonstrated using various tests carried out both on the pure plant extracts and on plant extracts that had been rendered insoluble. These studies, carried out in March 2007, were carried out on Cosmos, Quebracho, and Pernambuco.

Six samples were used; they had the following references:
Pure Cosmos extract—batch 1024;
Pure Quebracho extract—batch 8636;
Pure Pernambuco extract—batch 05-33;
Dispersed Cosmos extract—6IT06/F001
Dispersed Quebracho extract—6IT06/F004;
Dispersed Pernambuco extract—6IT06/F002.

The aim of these tests was to demonstrate the anti-radical activity of pure plant extracts in the powder form as well as the anti-radical activity of those same extracts associated with an insoluble mineral substrate and dispersed in carnation oil that is routinely used in the cosmetic compositions of makeup products.

Materials and Methods

The activity of the pure extracts was studied by means of two biochemical tests: one was based on the reduction of 2,2-diphenyl-1-picrylhydrazyl (DPPH) by the anti-oxidants, and the other was based on the measurement of hydrogen peroxide ($H_2O_2$) in the reaction media. $H_2O_2$ is trapped by a specific reagent, "AmplexRed". 2,2-diphenyl-1-picrylhydrazyl (DPPH) is a stable radical compound that is reduced to 1,1-diphenyl-2-picrylhydrazine by anti-oxidants. This reduction is followed by a color change in the DPPH solution (optical density measurement).

AmplexRed is a compound which reacts in a stoichiometric manner with $H_2O_2$, producing a fluorescent red compound, resofurin, which can be measured by fluorescence. This test can detect small quantities of $H_2O_2$.

The pure extracts as well as the anti-oxidant references (α-tocopherol and BHA: butylated hydroxyanisole for DPPH, BHA alone for AmplexRed) were dissolved in ethanol. Controls using ethanol alone were produced in order to verify the absence of interference of this solvent.

Pure Extracts: DPPH Test

The products for this test were tested starting from a concentration of 1 mg/ml in a power of ten series. The alpha-tocopherol positive control was tested at a concentration of 0.1 µM [micromolar] and the BHA was tested at a concentration of 50 µM.

Pure Extracts: $H_2O_2$/AmplexRed

The products for this test were tested starting from a concentration of 1 µg/ml in a power of ten series. The BHA positive control was tested at concentrations of 50 µM and 500 µM.

Study of the activity of extracts associated with an insoluble mineral substrate dispersed in carnation oil were carried out using a lipid peroxidation test on irradiated skin explants. This test, which was carried out by applying the products topically, meant that the effects of non-hydrosoluble extracts could be studied in vitro.

The cytotoxicity had already been checked using a test with MTT (3-(4,5-dimethylthiazol-2-yl)-2,5-diphenyl tetrazolium bromide (tetrazolium salt)) in order to determine the concentrations to be tested.

Upon receipt, the skin explants were cut and placed in culture.

The test products or the reference (positive control=BHA) were then applied to the surface of the explants in a quantity of 5 mg/cm$^2$ [milligrams/square centimeter] and the explants were placed in an incubator for 24 h [hours] at 37° C. in the presence of 95% air and 5% $CO_2$. The pieces of control skin did not undergo any treatment.

After incubation and washing, the explants for each series were exposed to irradiation using ultraviolet A and B (UVA+B) radiation. Irradiation was carried out using a SOL500 Sun Simulator lamp with an H2 filter and the exposure conditions were as follows:

UVA+B filter:
UVA: power 11.5 mW/cm$^2$ [milliwatt/square centimeter] i.e. 678.6 mJ/cm$^2$/minute [millijoule/square centimeter/minute];
UVB: power 0.78 mW/cm$^2$, i.e. 47.1 mJ/cm$^2$/minute;
Irradiation period: 21 minutes;
i.e. approximately 1 J/cm$^2$ of UVB and 14 J/cm$^2$ of UVA.

Three other untreated control explants were kept away from the light. Following irradiation, the explants were again incubated for 24 h.

The epidermis was then extracted and the viability of the cells was evaluated using MTT reduction.

The lipids of the epidermis were extracted with a methanol/chloroform mixture before assaying lipid peroxidation using a specific kit, in particular using the PeroxiDetect kit (Sigma PD1). The results are expressed in nmoles of lipid peroxides per volume of sample.

Results

Pure Extracts

Pure Extracts: DPPH Test

|  | Treatment | % control (OD) | Activity* | CI50 |
|---|---|---|---|---|
| Ethanol control | / | 100 | − | / |
| Tocopherol | 0.1 µM | 9 | ++ | / |
| BHA | 50 µM | 74 | +/− | / |
| Cosmos | 1 mg/ml | 23 | ++ | 0.1 mg/ml |
|  | 0.1 mg/ml | 51 | + |  |
|  | 0.01 mg/ml | 97 | − |  |
| Quebracho | 1 mg/ml | 121 | − | 0.06 mg/ml |
|  | 0.1 mg/ml | 24 | ++ |  |
|  | 0.01 mg/ml | 74 | +/− |  |
| Pernambuco | 1 mg/ml | 25 | ++ | 0.07 mg/ml |
|  | 0.1 mg/ml | 10 | ++ |  |
|  | 0.01 mg/ml | 74 | +/− |  |

++: large reduction more than 50%,
+: 50% reduction,
+/−: 25% reduction
−: absence of reduction As was expected the negative control, pure ethanol, did not reduce the DPPH. The references, in particular the tocopherol, clearly reduced the DPPH. These negative and positive controls produced the anticipated results and thus meant that the test could be validated. The 3 pure extracts tested in the range of 1 mg/ml to 0.01 mg/ml reduced the stable radical compound DPPH in a dose-dependent manner, meaning that the DPPH reduction was different depending on the dose.

The approximate values for CI50 for Cosmos, Quebracho and Pernambuco were respectively 0.1 mg/ml, 0.06 mg/ml and 0.07 mg/ml.

Pure Extracts: $H_2O_2$/AmplexRed Test

| Treatment | | % control (fluorescence intensity) | Activity* | CI50 |
|---|---|---|---|---|
| Ethanol control | Pure ethanol | 100 | − | |
| BHA | 50 μM | 38 | ++ | |
| | 500 μM | 34 | ++ | |
| Cosmos | 0.1 μg/ml | 98 | − | 7.4 μg/ml |
| | 1 μg/ml | 80 | +/− | |
| | 10 μg/ml | 80 | ++ | |
| Quebracho | 0.1 μg/ml | 74 | +/− | 0.7 μg/ml |
| | 1 μg/ml | 40 | ++ | |
| | 10 μg/ml | 42 | ++ | |
| Pernambuco | 0.1 μg/ml | 71 | +/− | 0.8 μg/ml |
| | 1 μg/ml | 44 | + | |
| | 10 μg/ml | 72 | +/− | |

++: strong reduction more than 50%,
+: 50% reduction,
+/−: 25% reduction
−: absence of reduction The positive and negative controls provided the expected results. In particular, BHA very substantially reduced the quantity of free $H_2O_2$, revealed by the AmplexRed reaction (respectively 35% and 38% of the control). The test was thus considered to be valid.

The 3 extracts, tested between 0.1 μg/ml and 10 μg/ml, reduced the quantity of free $H_2O_2$ revealed by the AmplexRed reaction in a dose-dependent manner.

The approximate values of CI50 for Cosmos, Quebracho and Pernambuco were respectively 7.4 μg/ml, 0.7 μg/ml and 0.8 μg/ml.

Conclusion for the two tests on the pure extracts: the three test extracts had an advantageous anti-radical activity since they were active at low concentrations.

According to the CI50, it can be concluded that the Quebracho and Pernambuco extracts have comparable anti-radical power that is greater than that of the Cosmos extract.

Extracts Associated with an Insoluble Mineral Substrate: Effect on Lipid Peroxidation Irradiation by UV caused a significant increase in the quantity of lipid peroxides in the proportions normally obtained in the laboratory without modifying viability. It should be noted that the vehicle used to dissolve the products (carnation oil) did not interfere with the assay.

The treatment of skin explants with the reference greatly reduced the production of lipid peroxides after irradiation. This result was expected and validated the test.

The Cosmos plant extract, tested in a concentration of 5%, 1% and 0.2%, allowed a significant reduction in the concentration of lipid peroxides. In a concentration of 1%, the Cosmos plant extract reduced the production of lipid peroxides after irradiation by close to 50%.

The Pernambuco plant extract, tested at 50%, 10% and 2%, significantly reduced the production of lipid peroxides. At 50% and 10%, the product was still slightly pro-oxidizing. At 2%, it had reduced the production of lipid peroxides after irradiation by approximately 50%.

The Quebracho plant extract tested at 50% did not show any effect, but when tested at 10% and 2%, it significantly reduced the production of lipid peroxides. At 10%, it had reduced the production of lipid peroxides after irradiation by approximately 40%.

In conclusion, the Cosmos, Pernambuco and Quebracho plant extracts exhibited protective effects against the stress induced by UV irradiation by reducing the production of lipid peroxides. The effects of these products are visible at low concentration.

It is also interesting to note that the Cosmos plant extract in a concentration of 1% and the Pernambuco plant extract in a concentration of 2% retained a level of lipid peroxidation close to that of the non-irradiated control.

Conclusion

The various tests have demonstrated a significant anti-radical activity for the Cosmos, Quebracho and Pernambuco extracts whether in the pure form (DPPH and AmplexRed biochemical tests) or associated with an insoluble substrate (lipid peroxidation assay on irradiated skin explants).

As a consequence, association with a substrate does not alter the anti-radical properties of the plant extracts of natural origin.

2. Tests on the Composition Comprising the Plant Extract.

Following on from the results obtained on the Cosmos, Pernambuco and Quebracho extracts in the context of the tests described above, a test for the anti-radical activity of an eye shadow containing these extracts was developed. It was a lipid peroxidation test carried out on skin explants in August 2007.

The human skin explant model allows topical applying the products to allow an in vitro study of the effects of the finished products, here an eye shadow. Using A and B ultraviolet radiation (UVA+B) caused the production of reactive oxygen-containing species, i.e. oxygen-containing free radicals, present in the skin during exposure to the sun ($O_2$., OH., $H_2O_2$.). These oxygen-containing free radicals are partially responsible for the genetic damage (alteration to DNA) and the cellular damage (oxidation of proteins and lipids) encountered in the skin.

An increase in the quantity of oxygen-containing free radicals induces lipid peroxidation that gives rise to chain reactions inducing the formation of highly reactive species which perturb the biological functions of the membranes and lead to local phenomena of skin dryness and irritation. These direct oxygen-containing free radical effects can also be supplemented by adding various indirect effects which participate in accelerating ageing of the skin.

The aim of this study was to evaluate the anti-radical activity of an eye shadow containing plant extracts defined below, using a lipid peroxidation test on irradiated skin explants. The effects of this eye shadow were compared with an eye shadow containing no anti-radical active ingredients.

Materials and Methods

Biological Model:

Abdominal plastic surgery was carried out on a 45 year old woman (donor).

test medium: DMEM (Invitrogen 21969035), glutamine 2 mM, penicillin-streptomycin 50 IU/ml-50 μg/ml, 10% fetal calf serum.

Samples Used:

6YI07/B043: control eye shadow, with no colored plant extracts (replaced by a red pigment);

6YI07/B042: eye shadow containing 5% Quebracho plant extract, 5% Pernambuco extract and 5% Cosmos extract.

Treatment and Irradiation:

A conventional lipid peroxidation test was carried out on irradiated skin explants. This test, which was carried out by topical applying eye shadow, allowed the effects of the eye shadow to be studied in vitro.

On receipt, 4 cm² skin explants were cut out then placed under culture. The skin explants then received different treatments. Some received the control eye shadow, others received the "test" eye shadow containing the plant extracts, others received a sun cream with a sun protection factor of 20 (SPF20) acting as a positive control and others received no treatment (negative control).

The treatments (eye shadow or SPF20 sun cream) were applied in an amount of 5 mg/cm², and the explants were then placed in an incubator at 37° C. for 24 h in the presence of 95% air and 5% $CO_2$. After incubation and washing, the explants for each series were exposed to irradiation of the A and B ultraviolet radiation type (UVA+B). Irradiation was carried out using a SOL500 Sun Simulator with an H2 filter and the exposure conditions were as follows:

UVA+B filter:

UVA: power 10 J/cm²;

UVB: power 1 J/cm².

Three other untreated control extracts were kept away from the light. Following irradiation, the explants were incubated again for 24 h.

After incubation, the surface of the explants was rinsed with PBS and for each explant, three 8 mm [millimeter] disks were punched out then incubated in sterile water at 62° C. for 2 minutes, in order to separate the epidermis from the dermis. An additional 8 mm disk was punched out for each treatment in order to evaluate the viability of the cells using a MTT reduction test (standard protocol).

Lipid Peroxidation Test

The epidermis was then extracted and the viability of the cells was evaluated by MTT reduction. The epidermal lipids were extracted with a methanol/chloroform mixture (standard protocol) before assaying the lipid peroxidation using a specific PeroxiDetect kit (Sigma PD1), using the procedure recommended by the supplier. The results are expressed in nmoles of lipid peroxides per volume of sample (30 μl), then converted into a protection percentage (%) compared with the irradiated control explant.

Data Treatment

The crude count data were transferred and processed using PRISM software (Graph Pad Software). Inter-group comparisons were made using variance analysis (ANOVA) followed by a multiple Dunnett comparison test.

The percentage protection was calculated using the formula:

$$P \% \text{ of protection} = \frac{(\text{control} + UV - \text{treated} + UV) \times 100}{(\text{control} + UV - \text{control} - UV)}$$

Results

The results of this test are shown in the table and graph below:

| Treatment | nmoles of peroxides | % control | % protection | P % of FAR* protection vs control FAR* |
|---|---|---|---|---|
| Control without UV (−) | 4.85 | 60 | 100 | — |
| Control with UV (+) | 8.12 | 100 | 0 | — |
| SPF20 sun cream | 2.92 | 36 | 159 | — |
| Control ES** | 6.06 | 75 | 63 | — |
| Test ES (with CVE***) | 4.60 | 57 | 108 | 121 |

*FAR: free anti-radicals;
**ES: eye shadow;
***CVE: colored plant extracts

Irradiation with UV caused a significant increase in the quantity of lipid peroxides in proportions normally obtained in the laboratory. Treating the skin explants with SPF20 sun cream (positive control) greatly reduced the production of lipid peroxides after irradiation (36% compared with the control+UV). This result was expected and validated the test.

Applying the control eye shadow (control ES) to the surface of the explants significantly reduced the quantity of lipid peroxides following irradiation compared with the control which had been irradiated (75% of control with UV(+), p<0.05).

Applying eye shadow containing the plant extracts (test ES with CVE) to the surface of the explants allowed the quantity of lipid peroxides following irradiation to be substantially reduced and in a manner that was significantly different from the control receiving UV irradiation (57% of control with UV(+), p<0.05).

In conclusion, the control eye shadow (control ES) could slightly protect the skin from the effects of free radicals induced by UV irradiation. In contrast, the eye shadow containing the plant extracts (test ES) has a protective power against free radicals that is greater than that of the control eye shadow. Adding the plant extracts can thus accentuate the anti-radical power of the control eye shadow (see last column of table).

The tests detailed above demonstrate the anti-radical properties of the insoluble plant extracts of natural origin used in the cosmetic compositions of the invention. The insoluble form of these extracts is that used in the cosmetic composition according to the invention, in particular for the makeup products.

This novel technology applied to makeup products has many advantages. The development of these insoluble plant extracts of natural origin means that ranges of makeup can be developed that are very rich in phenolic compounds. These insoluble plant extracts of natural origin with anti-radical properties mean that products can be produced that are extremely rich in anti-oxidizing substances that are beneficial to protecting the epidermis, hair, and nails in particular.

The use of these insoluble plant extracts of natural origin in the cosmetic compositions of the invention conveys a natural image for the cosmetic composition while providing it with an anti-radical effect.

These insoluble plant extracts of natural origin also have the advantage of being capable of being readily incorporated into a large number of cosmetic compositions, in particular into anhydrous makeup formulations. The fact that the plant extracts of natural origin are rendered insoluble also means that the spectrum of action and of incorporation of such compounds into cosmetic compositions can be made broader.

These insoluble plant extracts of natural origin can readily be introduced into any of the galenical forms of cosmetic products, in particular into any of the known forms of makeup, because of their high degree of compatibility with these various galenical forms. The facility with which they can be introduced into the cosmetic compositions of the invention renders them capable of being used on a large scale.

SUSCEPTIBILITY OF INDUSTRIAL APPLICATION

The invention is of industrial application in the design and use of cosmetic products for topical use.

Figure 1:
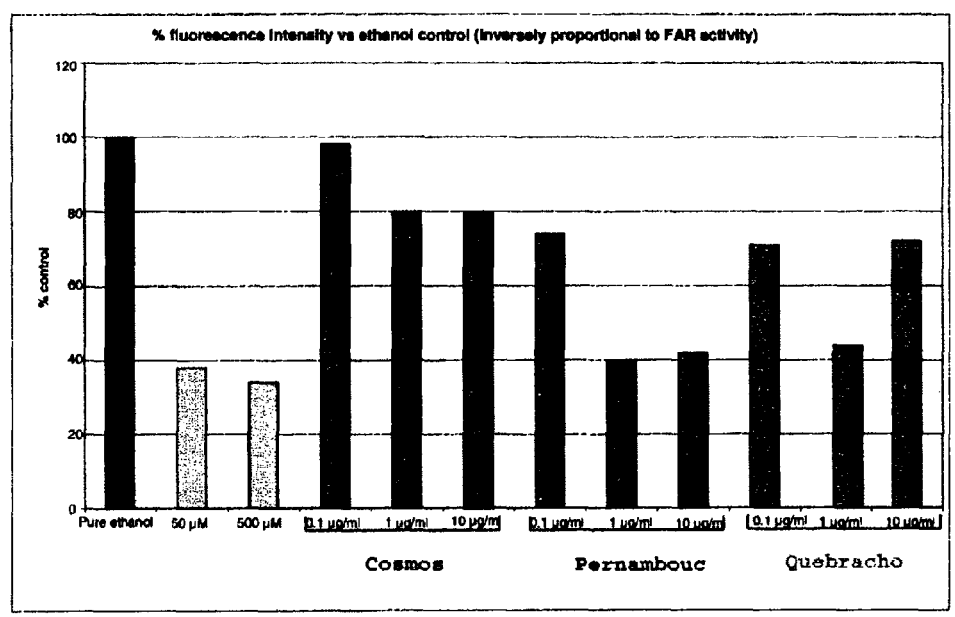
FIG. 1 is a graphical representation of the experimental results from the study of anti-radical activity showing the percent fluorescence intensity versus ethanol control of pure extracts, using a peroxide/AmplexRed test.
Figure 2:
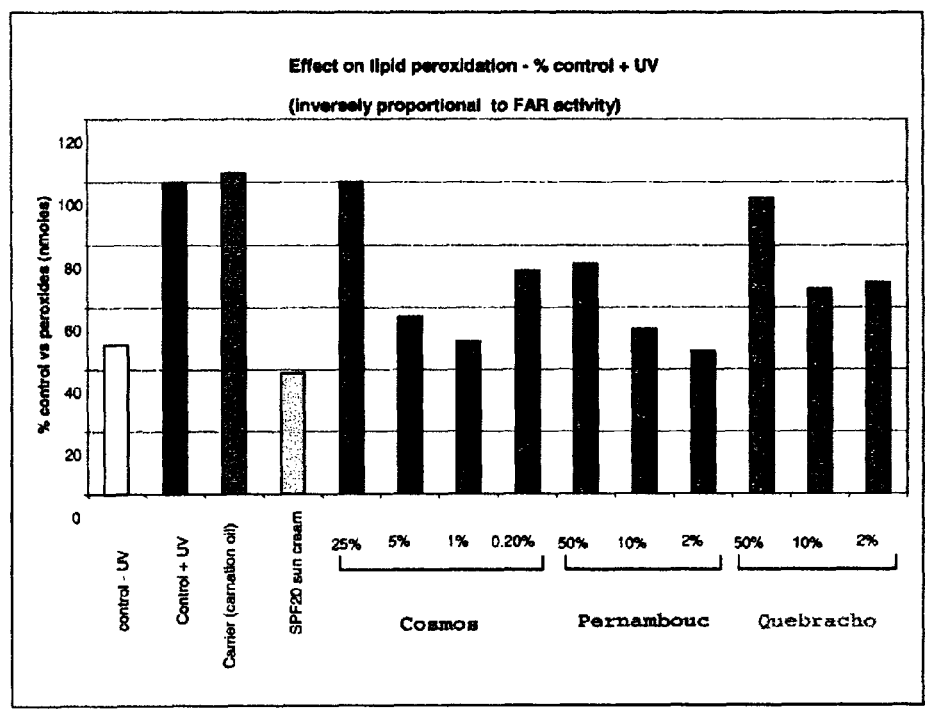
FIG. 2 is a graphical representation of the experimental results from the study of anti-radical activity showing activity of extracts associated with an insoluble mineral substrate, using a lipid peroxidation test on irradiated skin explants.
Figure 3:
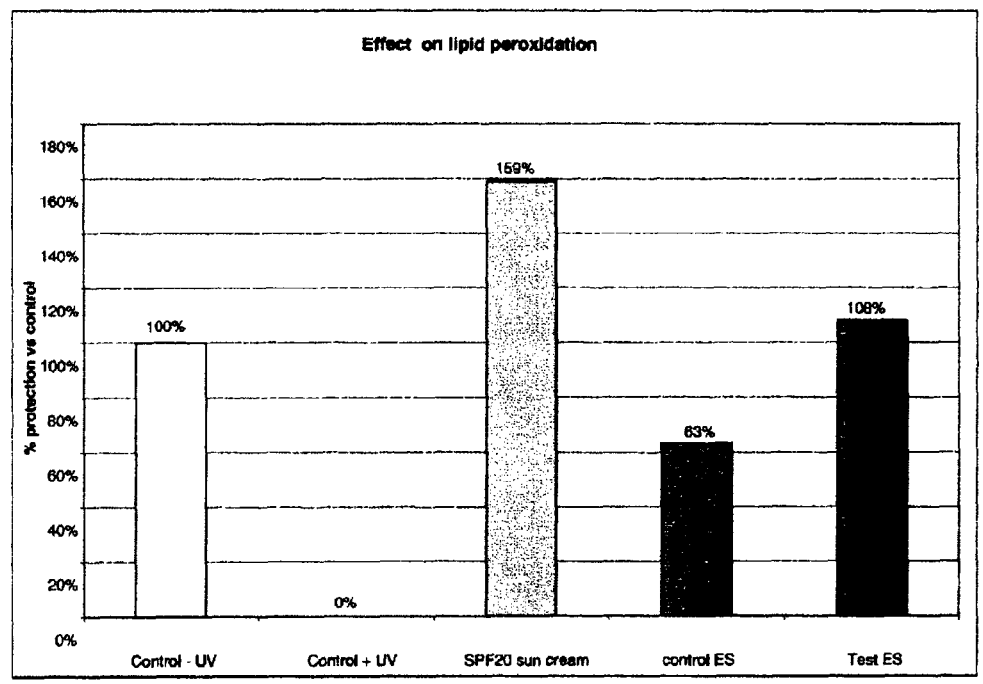
FIG. 3 is a graphical representation of the experimental results from the study of anti-radical activity of an eye shadow containing plant extracts, using a lipid peroxidation test on irradiated skin explants.

The invention claimed is:

1. A topical cosmetic composition consisting essentially of antioxidizing effective amounts of a cosmos extract and a pernambuco extract.

2. A topical cosmetic composition consisting essentially of antioxidizing effective amounts of a cosmos extract, a pernambuco extract and an extract selected from the group consisting of oak extract, sorghum extract and quebrancho extract.

* * * * *

UNITED STATES PATENT AND TRADEMARK OFFICE
CERTIFICATE OF CORRECTION

PATENT NO. : 8,475,848 B2  Page 1 of 1
APPLICATION NO. : 12/452458
DATED : July 2, 2013
INVENTOR(S) : Masson et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 280 days.

Signed and Sealed this
Eighth Day of September, 2015

Michelle K. Lee
*Director of the United States Patent and Trademark Office*